US011432929B2

(12) United States Patent
Elist

(10) Patent No.: US 11,432,929 B2
(45) Date of Patent: *Sep. 6, 2022

(54) PROSTHESIS FOR IMPROVED PENIS FUNCTION

(71) Applicant: James Elist, Beverly Hills, CA (US)

(72) Inventor: James Elist, Beverly Hills, CA (US)

(73) Assignee: Menova International, Inc., Beverly Hills, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 16/434,182

(22) Filed: Jun. 7, 2019

(65) Prior Publication Data

US 2020/0383788 A1    Dec. 10, 2020
US 2022/0015908 A9    Jan. 20, 2022

Related U.S. Application Data

(63) Continuation-in-part of application No. 15/905,652, filed as application No. PCT/US2016/020881 on
(Continued)

(51) Int. Cl.
*A61F 2/26*    (2006.01)
*A61F 5/41*    (2006.01)

(52) U.S. Cl.
CPC .................. *A61F 2/26* (2013.01); *A61F 5/41* (2013.01); *A61F 2220/0008* (2013.01); *A61F 2230/0069* (2013.01)

(58) Field of Classification Search
CPC ...... A61F 2/26; A61F 2/02; A61F 2/04; A61F 5/41; A61F 2005/415
See application file for complete search history.

(56) References Cited

U.S. PATENT DOCUMENTS 1,383,944 A    7/1921   Hart
2,899,957 A    8/1949   Briggs
(Continued)

FOREIGN PATENT DOCUMENTS

CN       1291874 A      3/1999
CN    101848688 A      9/2010
(Continued)

OTHER PUBLICATIONS

Written Opinion in International Patent Application No. PCT/US/2016/20881, dated May 12, 2016 (3 pages).
(Continued)

*Primary Examiner* — John P Lacyk
(74) *Attorney, Agent, or Firm* — Nixon Peabody LLP; Jeffrey L. Costellia

(57) ABSTRACT

A prosthesis is implanted subcutaneously within a human penis, the prosthesis forming sides of an elongated longitudinal modified cylindrical shape, the sides hinged along a common abutment therebetween. A sheath is mounted around the prosthesis' wall and a net sheeting is imbedded under the surface of the prosthesis' wall providing a means to secure the sides; restraining them to further secure a corpora cavernosa around the prosthesis is placed. When the penis is erect it grows in girth thereby causing the sides to diverge, forcing a press-rib against a deep dorsal vein of the penis, which results in restricting blood flow and maintaining erectile rigidity and duration.

19 Claims, 5 Drawing Sheets

Related U.S. Application Data

Mar. 4, 2016, now Pat. No. 10,350,070, which is a continuation of application No. 14/986,484, filed on Dec. 31, 2015, now Pat. No. 9,504,573.

(56) References Cited

U.S. PATENT DOCUMENTS

| | | | |
|---|---|---|---|
| 3,455,301 | A | 7/1969 | Clark |
| 3,893,456 | A | 7/1975 | Small |
| 3,987,789 | A | 10/1976 | Timm |
| 4,204,530 | A | 5/1980 | Finney |
| 4,267,829 | A | 5/1981 | Burton |
| 4,483,331 | A | 11/1984 | Trick |
| 4,523,584 | A | 6/1985 | Yachia et al. |
| 4,566,446 | A | 1/1986 | Fogarty |
| 4,589,405 | A | 5/1986 | Hemmeter |
| 4,602,625 | A | 7/1986 | Yachia |
| 4,628,914 | A | 12/1986 | Everson |
| 4,669,456 | A | 6/1987 | Masters |
| 4,773,403 | A | 9/1988 | Daly |
| 4,881,530 | A | 11/1989 | Trick |
| 4,942,886 | A | 7/1990 | Timmons |
| 4,982,731 | A | 1/1991 | Lue |
| 5,063,914 | A | 11/1991 | Cowen |
| 5,101,813 | A | 4/1992 | Trick |
| 5,250,020 | A | 10/1993 | Bley |
| 5,263,981 | A | 11/1993 | Polyak |
| 5,344,388 | A | 9/1994 | Maxwell |
| 5,445,594 | A | 8/1995 | Elist |
| 5,512,033 | A | 4/1996 | Westrum |
| D376,011 | S | 11/1996 | Nunokawa |
| 5,611,515 | A | 3/1997 | Benderev |
| 5,669,870 | A | 9/1997 | Elist |
| 5,895,424 | A | 4/1999 | Steele |
| 5,899,849 | A | 5/1999 | Elist |
| 6,015,380 | A * | 1/2000 | Subrini ............... A61F 2/26 600/38 |
| 6,475,137 | B1 | 11/2002 | Elist |
| 6,537,204 | B1 * | 3/2003 | Elist ............... A61F 2/26 600/40 |
| 6,749,558 | B1 | 6/2004 | Brintle |
| 7,584,757 | B2 | 9/2009 | Krakovsky |
| 7,628,812 | B2 | 12/2009 | Awengen |
| 8,986,193 | B1 | 3/2015 | Elist |
| 9,320,832 | B2 | 4/2016 | Joseph |
| 9,504,573 | B1 * | 11/2016 | Elist ............... A61F 2/26 |
| 10,350,070 | B2 * | 7/2019 | Elist ............... A61F 2/26 |
| 2003/0212463 | A1 | 11/2003 | Seo |
| 2014/0031619 | A1 | 1/2014 | Moon |

FOREIGN PATENT DOCUMENTS

| | | |
|---|---|---|
| CN | 103565572 A | 2/2014 |
| EP | 2 853 239 | 4/2015 |
| EP | 2853239 A1 | 4/2015 |
| JP | A 1992-501372 | 3/1992 |
| JP | 2015-507481 A | 3/2015 |
| WO | WO 99/44550 | 9/1991 |
| WO | WO-2005/065598 | 7/2005 |
| WO | WO 2005/065598 A1 | 7/2005 |
| WO | WO 2010/059064 A1 | 5/2010 |

OTHER PUBLICATIONS

Extended European Search Report in European Patent Application No. EP 16880189.2, dated Aug. 30, 2018 (10 pages).

Notice to Submit Response in Korean Patent Application No. KR 10-2017-7024560, dated Feb. 28, 2019 (4 pages).

First Office Action in Chinese Patent Application No. CN 2016800080126, dated Nov. 28, 2019 (7 pages).

Notice for Reasons of Refusal in Japanese Patent Application No. JP 2017-541114, dated Dec. 19, 2019 (4 pages).

Preliminary Office Action in Brazilian Patent Application No. BR 112018012587-3, dated May 12, 2020 (4 pages).

First Examination Report in Australian Patent Application No. AU 2016380684, dated Nov. 24, 2020 (5 pages).

Notice to Submit Response in Korean Patent Application No. KR 10-2019-70363245, dated May 14, 2021 (6 pages).

Notice for Reasons of Refusal in Japanese Patent Application No. JP 2020-157574, dated May 31, 2021 (4 pages).

Notice of Fulfillment Amendments in Qatari Patent Application No. QA/201806/00245, dated Feb. 3, 2022 (4 pages).

Notice to Submit Response in Korean Patent Application No. KR 10-2022-7003332, dated Mar. 7, 2022 (3 pages).

Mexican Office Action for Application No. MX/a/2018/008170, dated Apr. 29, 2022 (5 pages).

Kuwait Office Action for Application No. KW/P/2018/68, dated Apr. 18, 2022 (8 pages).

Canadian Office Action for Application No. 2976141, dated May 4, 2022 (3 pages).

* cited by examiner

PROSTHESIS FOR IMPROVED PENIS FUNCTION

CROSS-REFERENCE TO RELATED APPLICATIONS

This application is a continuation-in-part of U.S. application Ser. No. 15/905,652, filed on Feb. 26, 2018, which is a U.S. National Stage of International Application No. PCT/US2016/020881, filed on Mar. 4, 2016, which is a Continuation of application Ser. No. 14/986,484, filed on Dec. 31, 2015, each of which is hereby incorporated by reference herein in its entirety.

BACKGROUND OF THE INVENTION

Field of the Invention

This invention relates generally to surgical prostheses for the enhancement of appearance and operation of organs, and more particularly to a penile prosthesis enabling a damaged penis or poor penis function to be restored to a satisfactory sexual function and/or aesthetic appearance.

Description of Related Art

A prosthesis for implantation into a penis to provide rigidity and improve dimensions is known in the art. Such a prosthesis may include an elongated, malleable rod portion which is housed within a generally tubular, physiologically inert plastic body. The malleable rod portion enables the prosthesis to conform to a variety of shapes by bending or twisting it. During intercourse the prosthesis will maintain the penis in an erect state, and afterwards the penis may be positioned and maintained in a more convenient and comfortable position. Finney, U.S. Pat. No. 4,204,530 describes a prosthesis with a sleeve for increasing the penile diameter, and which includes a flexible sheet of soft, physiologically acceptable material, the sheet being of sufficient length when formed in the general shape of a cylindrical sleeve to extend from the glans penis to the base of the penis and of a width which is insufficient to completely encircle the penis, but is sufficient to cover the corpora cavernosa. Improved rod-type penile prostheses may have a relatively stiff proximal portion for positioning inside the corpora cavernosa adjacent the pubis for supporting the prosthesis, a longer relatively stiff distal portion for positioning in the corpora cavernosa of the pendulous penis, and a hinge separating the distal and proximal portions. Masters, U.S. Pat. No. 4,669,456 describes a penile prosthesis which comprises an elastomeric rod and a metal wire coil coaxially imbedded within at least a portion of the rod. Subrini, U.S. Pat. No. 6,015,380 describes a prosthesis which can be used to increase penile volume. Moreira de Azeredo, WO 86/01398 describes a penile rigidity prosthesis for the treatment of erectile impotence in men including at least one penile prosthesis comprising an elongated malleable cylindrical body adapted to be surgically placed in the corpora cavernosa.

The prior art teaches the use of a subcutaneously placed prostheses to rigidize the penis, but does not teach the use of certain contours that provide structural advantages nor a means for restricting flow through the dorsal vein, or a means for preventing axial movement or sliding of the prosthesis relative to the penis' long axis. The present invention fulfills these needs and provides further related advantages as described in the following summary.

SUMMARY OF THE INVENTION

The present invention teaches certain benefits in construction and use which give rise to the following objectives. A penile prosthesis may have a cylindrical, elongated body providing a wall thickness varying circumferentially from a maximum thickness at its top surface, to a minimum thickness along its bottom surface. The wall thickness may further vary longitudinally from a maximum thickness at a proximal end of the device to a minimum thickness at a distal end. The apparatus is preferably made of silicone rubber and has a length and size enabling subcutaneous implantation around the corpora cavernosa providing sufficient rigidity for enabling coitus while still being flexible enough to be conveniently positioned when the penis is flaccid.

An objective of the described and claimed prosthesis is to provide rigidity to the human penis so as to enable coitus.

A further objective is to provide an appropriate tapered appearance.

A still further objective is to enable surgical implantation without removal of existing organ portions or related tissues.

A yet further objective is to prevent the prosthesis from moving axially after being implanted.

A further objective is to provide a means for anchoring the distal end of the prosthesis.

An important objective is to stem the flow of blood out of the penis during coitus.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present prosthesis invention as described. In such drawings.

DETAILED DESCRIPTION OF THE INVENTION

Figure 9:
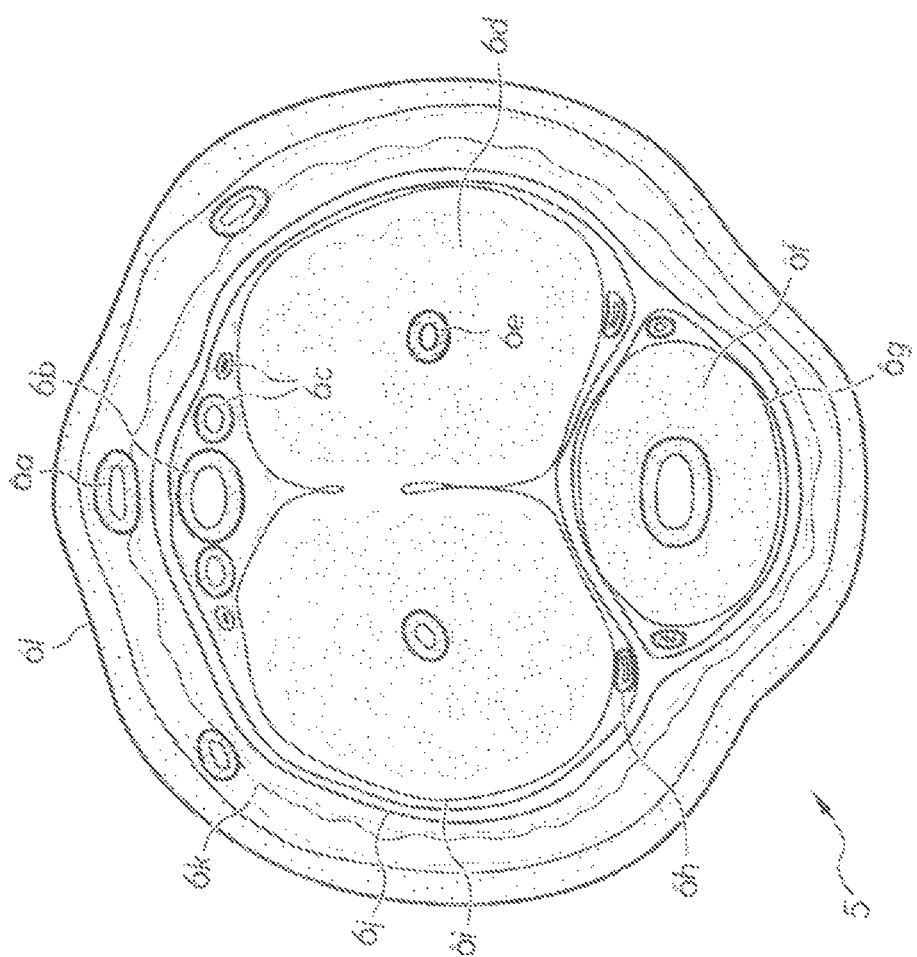
FIG. 9 is a cross-sectional view of a typical human penis.

The above described drawing figures illustrate the invention, a penile prosthesis 10, in at least one of its preferred embodiments, and is further defined in detail in this description. The penile prosthesis 10 may be made of silicone rubber or a like material and may be implanted subcutaneously into a human penis 5. FIG. 9 is a cross-section view illustrating the anatomy of penis 5 and showing in particular, the dorsal vein 6a, the deep dorsal vein 6b, the dorsal artery and nerve 6c, the corpus cavernosum penis 6d, the profunda artery 6e, the corpus spongiosum and urethra 6f, the tunica albuginea 6g, the intercavernous septum of buck's fascia 6h, the tunica albuginea of corpus cavernosum penis 6i, the"

buck's fascia 6*j*, the dartos fascia 6*k*, and the outer lying skin 6*l* which is the outer layer of penis 5 and under which penile prosthesis 10 is inserted.

Figure 1:
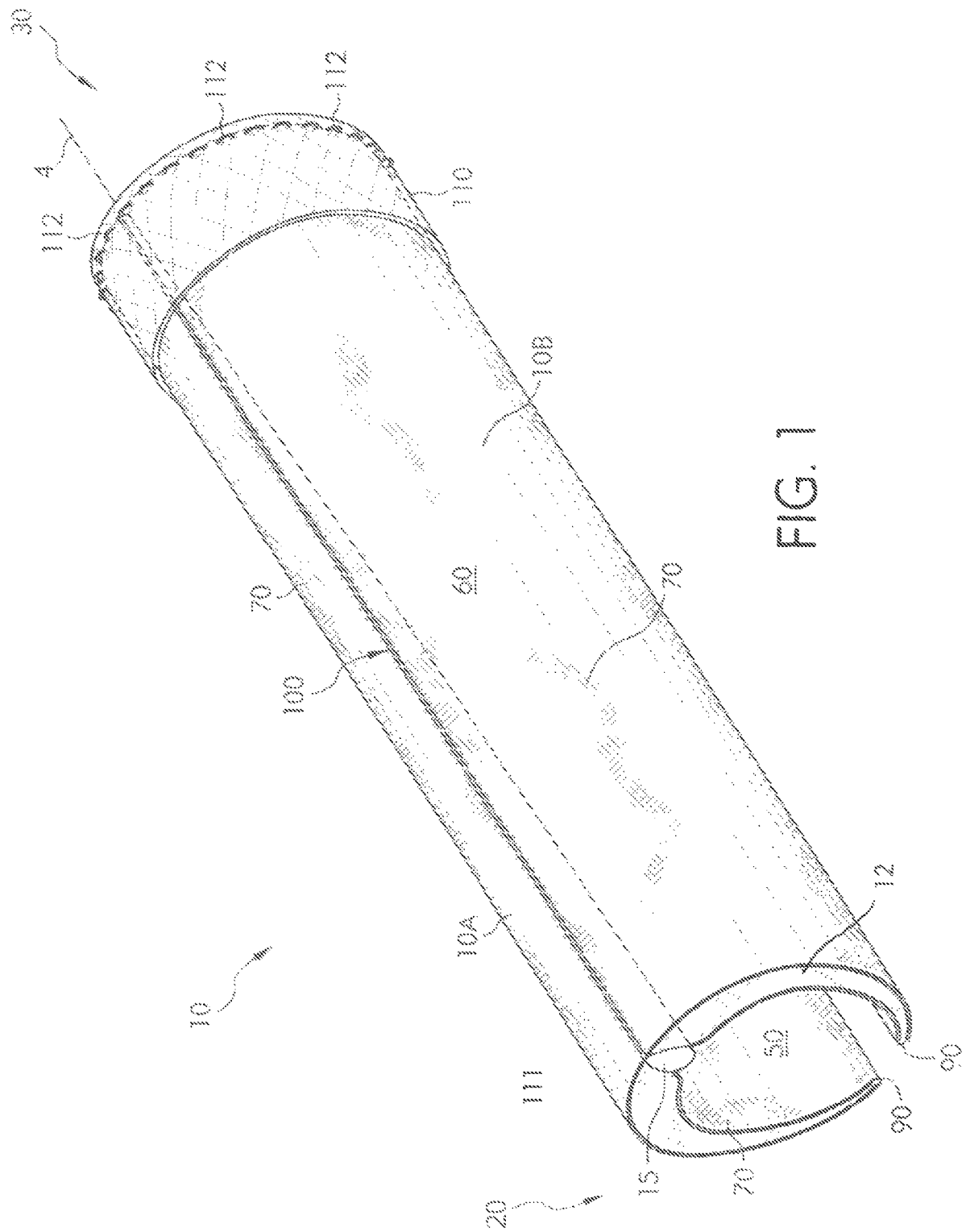
FIG. 1 is a proximal perspective view thereof.
Figure 2:
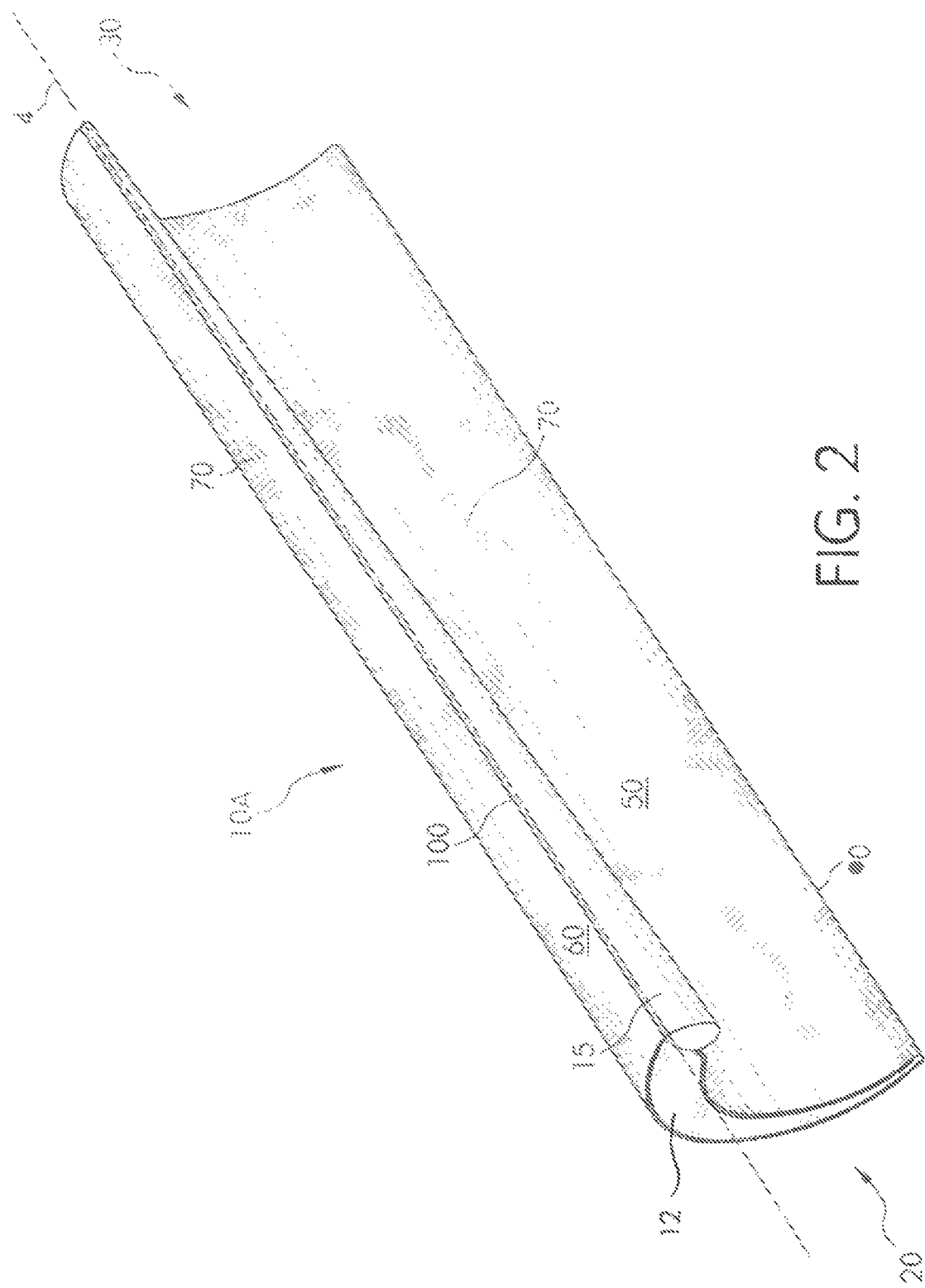
FIG. 2 is a proximal perspective view of one portion thereof.

Prosthesis 10 is well adapted by its elongated and longitudinally tapered modified cylindrical shape for subcutaneous implantation within human penis 5. Penile prosthesis 10 has opposing proximal 20 and distal 30 ends as shown in FIGS. 1 and 2, and is comprised of a wall 12 of a modified cylindrical shape whereby its portions 10A and 10B are flexibly joined and movable between relative convergent (FIGS. 1, 6 and 7) and divergent (FIG. 8) respective positions. The flexibly joining feature may be by any hinging means including a web of the same material as prosthesis 10. Any other hinging mechanism may be employed as well.

Figure 6:
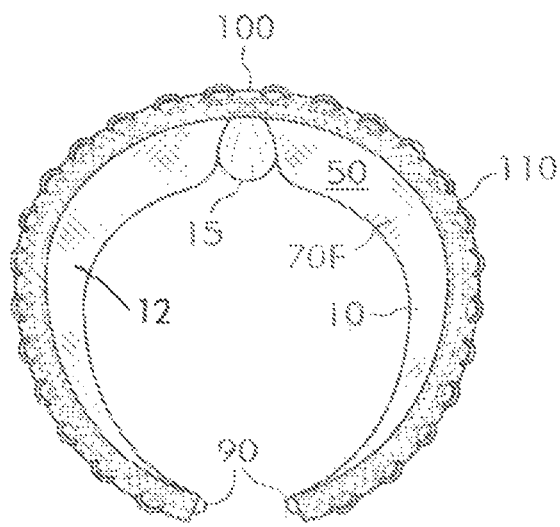
FIG. 6 is a distal end view of said prosthesis shown in a convergent attitude.
Figure 7:
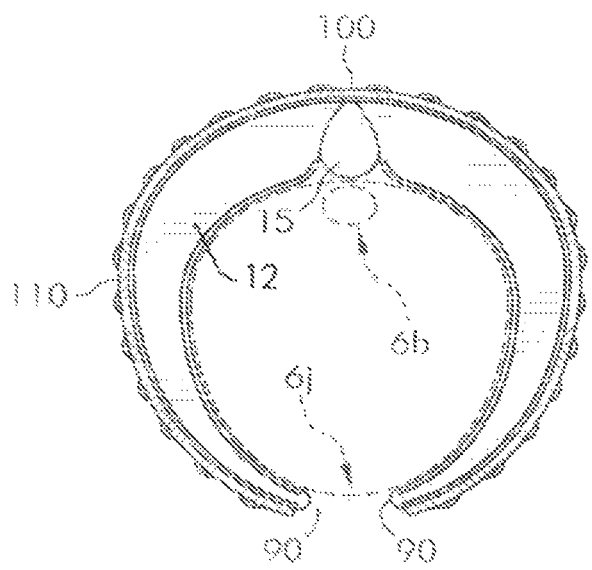
FIG. 7 is a proximal end view of said prosthesis shown in said convergent attitude.
Figure 8:
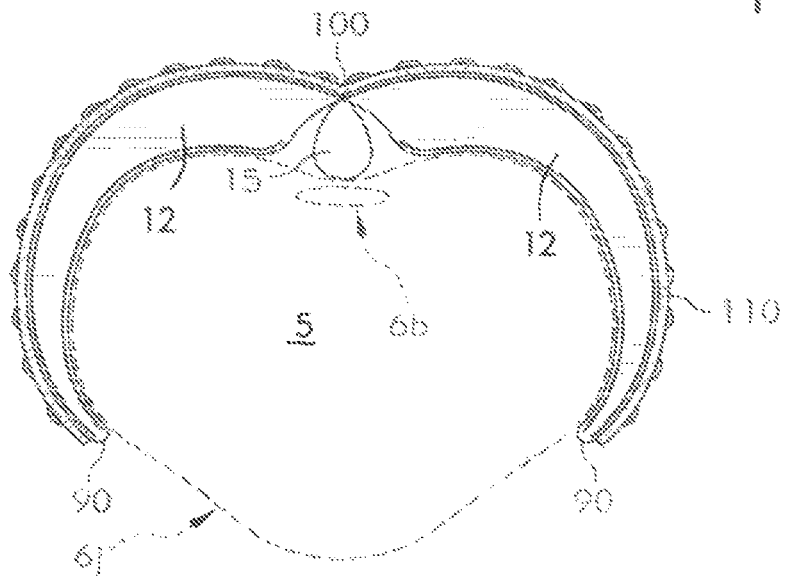
FIG. 8 is a proximal end view of said prosthesis shown in a divergent attitude.

In prosthesis 10 a press-rib 15 may be located between portions 10A and 10B as shown in FIGS. 6, 7 and 8 whereby press-rib 15 may be in a position for pressing downwardly onto a deep dorsal vein 6*b* of penis 5 as shown in FIG. 8. This may occur when engorged penis 5 becomes erect which drives portions 10A and 10B divergently as shown in FIG. 8 and which in turn causes press-rib 15 to bear down on vein 6*b* thereby restricting venus blood flow and enabling maintenance of an erect state of penis 5. Clearly, convergent and divergent attitudes of separate portions 10A and 10B are controlled by the erectile states of penis 5.

Figure 3:
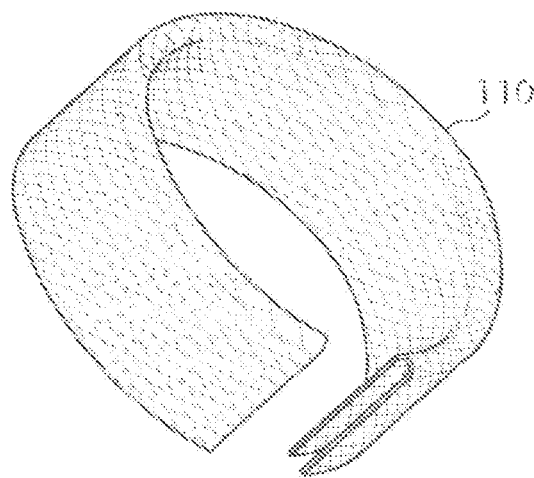
FIG. 3 is a distal perspective view of a sheath thereof.
Figure 4:
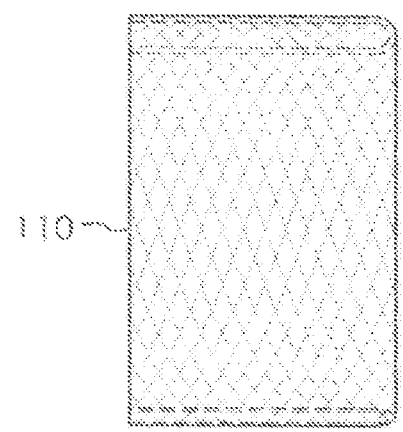
FIG. 4 is a side view of said sheath.
Figure 5:
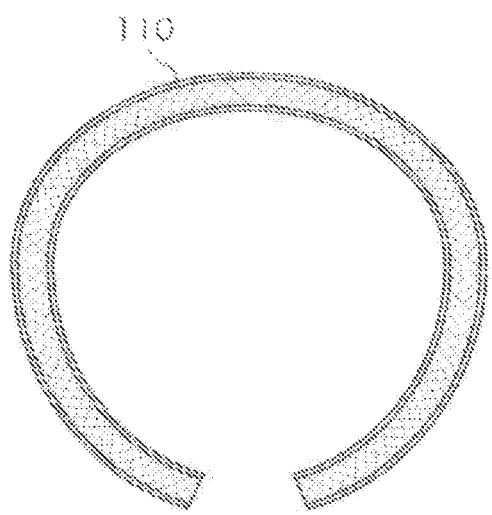
FIG. 5 is a proximal end view of said sheath.

As shown in 110, prosthesis 10 may have one or more sheaths 110 of the type shown in FIGS. 3, 4, and 5, or of similar shape and construction. Such a sheath 110 may be constructed of a sterile gauze fabric or similar material and may be mechanically secured around prosthesis 10 as shown. Prosthesis 10 may be distally positioned as shown in FIG. 1, or may be proximally positioned (not shown) or may be positioned in multiple locations around sheath 110. Such mechanical securement may include at least partially imbedding said sheath 110 within cylindrical wall 12. Other mechanical securements may be applied in addition or alternately, including the use of sutures 112, adhesives and other well-known surgical attachment prerogatives.

As shown in FIGS. 1 and 2, the thickness of cylindrical wall 12 may vary smoothly between proximal 20 and distal 30 ends, wherein said thickness of cylindrical wall 12 may be greatest at proximal end 20. The outside diameter of cylindrical wall 12 may vary smoothly between proximal and distal ends 20, 30 and may be greatest at proximal end 20. Clearly this configuration of cylindrical wall 12 is important for matching the anatomical aspects of penis 5 and also for structural integrity. As shown in FIGS. 1 and 6-8 cylindrical wall 12 must be longitudinally discontinuous along bottom edges 90 in order to be able to insert prosthesis 10 around penis 5 and also to enable divergence of portions 10A and 10B.

Prosthesis 10 may have a cylindrical body 10 of a selected longitudinal length aligned with the long axis 4 of penis 5, and may be open at both its proximal end 20 (nearest to the testacies), as well as at its opposite distal end 30 (nearest to the glans penis) as shown in FIG. 1. Prosthesis 10 may have an inside surface 50 and an outside surface 60 and may be formed as a single integral part with two joined portions 10A, 10B or alternately it may be formed as two separate portions 10A, 10B which may be later joined together as shown in FIG. 1. Portions 10A, 10B may be mirror images of each other as shown and may be joined prior to or during implantation into penis 5. The implantation process is taught in Finney, U.S. Pat. No. 4,202,530 which is hereby incorporated into the present application by reference. Thus, it is clear that prosthesis 10 can be formed to have a size and shape adapted for subcutaneous implantation below exterior skin 6*l* and in contact with buck's fascia 6*h*. Prosthesis 10 may extend from the base of penis 5 at its proximal end 20 to the glans penis at distal end 30. Both inside surface 50 and outside surface 60 may have a silicon net sheeting 70 imbedded just under these surfaces as shown in FIGS. 1 and 2, wherein net sheeting 70 may extend continuously over and/or under both portions 10A, 10B and thus may function as a hinge between the portions along abutment joining line 100. Portions 10A and 10B may therefore be moved between the two attitudes shown in FIGS. 7 and 8. Prosthesis 10, when in place around buck's fascia 6*j*, may be anchored using sutures joining net sheeting 70 to buck's fascia 6*j* or to tunica albuginea 6*g*, or both.

The thicker portion of wall 12 at proximal end 20, when placed adjacent to the base of the penis (not shown) provides the advantage of improved rigidity of prosthesis 10 and penis 5, and the thinner portion of wall 12 at distal end 30, adjacent to the glans penis (not shown), allows for improved movement of the glans penis for more convenient coital adjustment. The uniform taper from proximal end 20 to distal end 30 provides improved flexibility of penis 5 when flaccid. The thicker wall 12 along joining line 100 provides greater structural strength where the highest compressive forces occur during coitus. The circumferential taper provides improved flexibility of penis 5 and a more natural penile conformation and appearance as well as improved blood flow since cylindrical wall 12 may be quite thin near the glans penis, distal end 30 as best shown in FIG. 2. The important overall result of the conformation of prosthesis 10 is that it uses a relatively small amount of material in its structure while achieving sufficient rigidity and blood flow. The use of net sheeting 70 provides a wide range of choices as to placement of sutures. The use of longitudinally separated portions 10A, and 10B facilitates implantation and provides the opportunity to use asymmetrical portions as may be necessary for repair of a damaged or a misshapen penis 5. The space between the bottom longitudinal edges 90 allows penis 5 to expand without restraint as shown in FIG. 8.

The interior space within cylindrical wall 12 is preferably oblate, as is the human penis 5 with height greater than width as shown in FIGS. 6 and 7 with a preferred ratio of height to width of approximately 1.12. It has been found that this form enables improved blood flow as well as a more comfortable fit to the shape of penis 5.

FIG. 6 shows prosthesis 10 as viewed from its proximal end 20 looking axially toward the distal end 30 while FIGS. 7 and 8 show prosthesis 10 as viewed from the distal end 30 looking axially toward the proximal end 20. In these two figures, deep dorsal vein 6*b* is shown in dashed lines as located under press-rib 15 wherein FIG. 7 represents prosthesis 10 with a flaccid penis 5 while FIG. 8 represents an erect or engorged penis 5. It is shown that press-rib 15 compresses deep dorsal vein 6*b* to slow outward venus blood flow during an erect penis 5.

While the invention has been described with reference to preferred embodiments, it is to be understood by those skilled in the art that the invention is not limited thereto. Rather, the scope of the invention is to be interpreted only in conjunction with the appended claims.

What is claimed is:

1. A prosthesis adapted for subcutaneous implantation within a human penis having opposing proximal and distal ends, wherein said prosthesis comprises a substantially cylindrical wall wherein portions of said wall are adapted to be movable relative to each other between relative convergent and divergent positions; and at least one sheath secured to the wall.

2. The prosthesis of claim 1 wherein a press-rib located between two of said portions is positioned for pressing against a deep dorsal vein of said penis when said prosthesis is subcutaneously implanted within said human penis.

3. The prosthesis of claim 1 wherein said at least one sheath is at least partially imbedded within said wall.

4. The prosthesis of claim 1 wherein a thickness of said wall diminishes smoothly between said proximal and distal ends and wherein said thickness of said wall is greatest at said proximal end.

5. The prosthesis of claim 1 wherein an outside diameter of said wall diminishes smoothly between said proximal and distal ends and wherein said diameter of said wall is greatest at said proximal end.

6. The prosthesis of claim 1 wherein said wall is longitudinally discontinuous.

7. The prosthesis of claim 1 further comprising a net sheeting imbedded under a surface thereof.

8. The prosthesis of claim 7 wherein said net sheeting is functional as a hinge between said portions of said wall.

9. The prosthesis of claim 1 wherein an interior surface of said wall defines an oblate space there below.

10. The prosthesis of claim 1 wherein the sheath comprises a fabric material.

11. The prosthesis of claim 1 wherein the at least one sheath includes a gauze layer.

12. A prosthesis adapted for subcutaneous implantation within a human penis having opposing proximal and distal ends, wherein said prosthesis comprises a substantially cylindrical wall wherein portions of said wall are adapted to be movable relative to each other between relative convergent and divergent positions; and at least one fabric piece positioned at a location at the wall and configured to be sutured to the human penis at a corresponding location.

13. The prosthesis of claim 12 wherein the at least one fabric piece is a gauze fabric.

14. The prosthesis of claim 12 wherein the at least one fabric piece is a sheath.

15. A method for improving penis function using a prosthesis, the method comprising:

subcutaneous implanting the prosthesis within a human penis, the prosthesis having opposing proximal and distal ends, the prosthesis including a substantially cylindrical wall wherein two portions of said wall are adapted to be movable relative to each other between relative convergent and divergent positions; and causing a third portion of the wall located between said two portions to press against a deep dorsal vein of said human penis, wherein the third portion is a press-rib.

16. The method of claim 15 wherein a thickness of said cylindrical wall diminishes smoothly between said proximal and distal ends and wherein said thickness of said cylindrical wall is greatest at said proximal end.

17. The method of claim 15 wherein the press-rib located is positioned for pressing against the deep dorsal vein of said penis when said prosthesis is subcutaneously implanted within said human penis.

18. The method of claim 15 wherein the prosthesis has a net sheeting imbedded under a surface thereof.

19. The method of claim 18 wherein said net sheeting is functional as a hinge between said portions of said wall.

* * * * *